United States Patent [19]

Solomon et al.

[11] Patent Number: 4,666,914

[45] Date of Patent: May 19, 1987

[54] ANTI-INFLAMMATORY AND ANTI-ALLERGIC SUBSTITUTED-2,3-DIHYDRO-6-(HYDROXY)PYRIMIDO[2,1-F]-PURINE-4,8(1H,9H)-DIONES

[75] Inventors: Daniel M. Solomon, Edison; James J. Kaminski, Long Valley; David J. Conn, Somerville, all of N.J.

[73] Assignee: Schering Corporation, Kenilworth, N.J.

[21] Appl. No.: 732,994

[22] Filed: May 13, 1985

[51] Int. Cl.[4] .................. A61K 31/505; A61K 31/52; C07D 473/28; C07D 487/14
[52] U.S. Cl. ..................................... 514/267; 544/251
[58] Field of Search ...................... 544/251, 257, 265; 514/267

[56] References Cited

U.S. PATENT DOCUMENTS

| | | | |
|---|---|---|---|
| 3,862,189 | 1/1975 | Schwender | 544/265 X |
| 4,457,919 | 7/1984 | Simon et al. | 544/265 X |
| 4,460,590 | 7/1984 | Möller | 544/265 X |
| 4,569,936 | 2/1986 | Blythin | 514/267 |

OTHER PUBLICATIONS

Fieser, et al., "Reagents for Organic Synthesis", John Wiley & Sons, New York, (1967), pp. 588–589.
Fieser, et al. "Reagents for Organic Synthesis", John Wiley & Sons, New York, (1974), p. 293.

*Primary Examiner*—Donald G. Daus
*Assistant Examiner*—Diana G. Rivers
*Attorney, Agent, or Firm*—Stephen I. Miller; James R. Nelson

[57] ABSTRACT

Substituted 2,3-dihydro-6-(hydroxy)pyrimido[2,1-f]purine-4,8(1H,9H)-diones their tautomers and salts, are anti-inflammatory and anti-allergy agents.

Methods for their preparation and use are described.

24 Claims, No Drawings

ANTI-INFLAMMATORY AND ANTI-ALLERGIC SUBSTITUTED-2,3-DIHYDRO-6-(HYDROXY)-PYRIMIDO[2,1-F]-PURINE-4,8(1H,9H)-DIONES

BACKGROUND OF INVENTION

The present invention relates to substituted 2,3-dihydro-6-(hydroxy)pyrimido[2,1-f]purine-4,8(1H, 9H)-diones and tautomers thereof. These compounds are useful as anti-inflammatory agents for treating inflammatory conditions such as arthritis, spondylitis, and tendonitis in mammals. Also these compounds are useful as anti-allergy agents for treating allergy caused diseases.

SUMMARY OF INVENTION

In a composition of matter aspect, the invention relates to compounds having the structural formula I

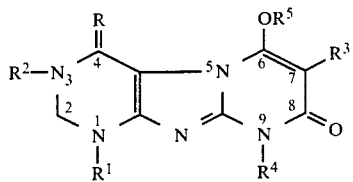

their tautomers, pharmaceutically acceptable salts or hydrates wherein $R^1$ and $R^2$ are independently selected from hydrogen, cycloalkyl having from 3 to 8 carbon atoms, phenyl, substituted phenyl, lower alkyl [which may be substituted with cycloalkyl having from 3 to 8 carbon atoms, phenyl, thienyl and substituted phenyl];

$R^3$ is hydrogen, formyl, cycloalkyl having from 3 to 8 carbon atoms, alkenyl having from 2 to 8 carbon atoms which alkenyl may be substituted with up to 6 fluorines, alkynyl having from 3 to 8 carbon atoms, cycloalkenyl having from 5 to 8 carbon atoms, acyloxyalkyl having from 2 to 12 carbon atoms, $X-R^6$ [wherein X is O, N or S and $R^6$ is phenyl, substituted phenyl or lower alkyl (which may be substituted with cycloalkyl having from 3 to 8 carbon atoms or phenyl)], -alkylY-$C_pH_{2p+1}$ [wherein the alkyl portion has 1 to 6 carbon atoms, p is an integer from 0 to 4, and Y represents CO, O, S, $S^+-O^-$, $SO_2$ or $-NC_rH_{2r+1}$ wherein r is an integer from 0 to 4], $-(CH_2)_nCONR^7R^8$ [wherein $R^7$ and $R^8$ are independently hydrogen or lower alkyl and n is an integer from 0 to 6], $-(CH_2)_mC(O)OR^9$ [wherein $R^9$ is hydrogen, lower alkyl or a pharmaceutically acceptable metal or amine cation and m is an integer from 0 to 6], phenyl, substituted phenyl, lower alkyl [which may be substituted with hydroxy, sulfhydryl, cyano, amino, halo, cycloalkyl having from 3 to 8 carbon atoms, phenyl, thienyl and substituted phenyl];

$R^4$ is hydrogen, phenyl, thienyl, substituted phenyl, pyridyl, lower alkyl [which may be substituted with cycloalkyl having from 3 to 8 carbon atoms, phenyl, pyridyl, thienyl or substituted phenyl]; and $R^5$ is hydrogen, alkyl having from 1 to 4 carbon atoms or a pharmaceutically acceptable metal or amine cation.

Preferred embodiments of the present invention relate to compounds having the structural formula I and the pharmaceutically acceptable salts thereof, wherein $R^1$ and $R^2$ are independently selected from alkyl of 1 to 4 carbon atoms;

$R^3$ is hydrogen, alkenyl having from 2 to 8 carbon atoms which alkenyl may be substituted with up to 6 fluorines, alkynyl having from 3 to 8 carbon atoms, cycloalkenyl having from 5 to 8 carbon atoms or lower alkyl which may be substituted with phenyl; $R^4$ is lower alkyl which is substituted with either phenyl, thienyl or substituted phenyl; and $R^5$ is hydrogen or a pharmaceutically acceptable cation.

More preferred values for $R^1$ and $R^2$ are alkyl of 1 to 3 carbon atoms. Most preferably $R^1$ and $R^2$ are methyl.

More preferred values for $R^3$ are hydrogen, alkenyl having from 3 to 8 carbon atoms which alkenyl may be substituted with up to 6 fluorines, alkynyl having from 3 to 8 carbon atoms, cycloalkenyl having from 5 to 8 carbon atoms and lower alkyl which may be substituted with phenyl. Most preferably $R^3$ is hydrogen, methyl, n-propyl, propargyl [$-CH_2C\equiv CH$], allyl, trans-2-butenyl, 2-cyclohexenyl, prenyl [$-CH_2CH=C(CH_3)_2$], $-CH_2CH=C(CF_3)CH_3$, $-CH_2CH=C(CF_3)_2$ or benzyl.

More preferred values for $R_4$ are benzyl, 2-thienylmethyl and substituted benzyl. Most preferably $R^4$ is 2-thienylmethyl, benzyl or p-fluoro-benzyl.

More preferred values for $R^5$ are hydrogen or a pharmaceutically acceptable metal cation, most preferably the sodium cation.

The preferred species having structural formula I are as follows:

9-benzyl-2,3-dihydro-1,3-dimethyl-6-hydroxy-7-(propyl)pyrimido[2,1-f]purine-4,8 (1H,9H)-dione. m.p. 177°–178.5° C.;

2,3-dihydro-1,3-dimethyl-9-(4-fluorobenzyl)-6-hydroxy-7-(propyl)pyrimido-[2,1-f]purine-4,8(1H,9H)-dione, m.p. 139°–140.5° C. (dec);

9-benzyl-2,3-dihydro-1,3-dimethyl-6-hydroxy-7-(3-methyl-2-butenyl)pyrimido[2,1-f]purine-4,8(1H,9H)-dione, m.p. 153°–154.5° C.;

9-benzyl-2,3-dihydro-1,3-dimethyl-6-(hydroxy)-pyrimido[2,1-f]purine-4,8(1H,9H)-dione, m.p. 176°–182° C.;

2,3-dihydro-1,3-dimethyl-9-(4-fluorobenzyl)-6-hydroxy-7-(3-methyl-2-butenyl)pyrimido[2,1-f]purine-4,8(1H,9H)-dione, m.p. 188°–188.5° C.;

9-benzyl-2,3-dihydro-1,3-dimethyl-6-hydroxy-7-(methyl)pyrimido[2,1-f]purine-4,8(1H,9H)-dione, m.p. 222°–224° C.;

2,3-dihydro-1,3-dimethyl-9-(4-fluorobenzyl)-6-(hydroxy)pyrimido[2,1-f]purine-4,8(1H,9H)-dione, m.p. 287°–290° C. (dec);

7,9-dibenzyl-2,3-dihydro-1,3-dimethyl-6-(hydroxy)-pyrimido[2,1-f]purine-4,8(1H,9H)-dione, m.p. 176°–179° C.;

9-benzyl-2,3-dihydro-1,3-dimethyl-7-formyl-6-(hydroxy)pyrimido[2,1-f]purine-4,8(1H,9H)-dione, m.p. 325°–326° C. (dec);

2,3-dihydro-1,3-dimethyl-9-(4-fluorobenzyl)-6-hydroxy-7-(2-propenyl)pyrimido[2,1-f]purine-4,8(1H,9H)-dione, m.p. 131.5°–133° C. (dec);

9-benzyl-2,3-dihydro-1,3-dimethyl-7-(2-propynyl)-6-(hydroxy)pyrimido[2,1-f]purine-4,8(1H,9H)-dione. m.p. 163°–164° C.;

9-benzyl-7-(trans-2-butenyl)-2,3-dihydro-1,3-dimethyl-6-(hydroxy)pyrimido[2,1-f]purine-4,8(1H,9H)-dione, m.p. 180°–183° C.;

9-benzyl-7-(3-cyclohexenyl)-2,3-dihydro-1,3-dimethyl-6-(hydroxy)pyrimido[2.1-f]purine-4,8(1H,9H)-dione, m.p. 208°–210° C.;

9-benzyl-2,3-dihydro-1,3-dimethyl-7-(ethoxy carbonylmethyl)-6-(hydroxy)pyrimido[2,1-f]purine-4,8(1H,9H)-dione, m.p. 148°–150° C.;

2,3-dihydro-1,3-dimethyl-9-(2-thienylmethyl)-6-hydroxy-7-propyl-pyrimido[2,1-f]purine-4,8(1H,9H)-dione, m.p.186°–188° C.; and 2,3-dihydro-1,3-dimethyl-9-(4-methoxybenzyl)-6-hydroxy-7-(3-methyl-2-butenyl)pyrimido[2,1-f]purine-4,8(1H,9H)-dione, m.p.157°–159° C.

The above species are also preferred in the form of their sodium salts.

When utilized herein and in the appended claims the below listed terms, unless specified otherwise, are defined as follows:

halogen means fluorine, chlorine, bromine and iodine; lower alkyl means straight or branched chain alkyls of 1 to 6 carbons, e.g. methyl, ethyl, propyl, ispropyl, butyl, t-butyl, pentyl, neopentyl, hexyl and the like; substituted phenyl, pyridyl, thienyl means phenyl, pyridyl, and thienyl substituted with 1 to 3 substituents independently selected from halogen, trifluoromethyl,

—CO$_2$H, hydroxy, —S(O)$_a$R$^{10}$ (wherein R$_{10}$ is lower alkyl and a is 0, 1 or 2), —OR$^{11}$ (wherein R$^{11}$ is lower alkyl, or

(wherein R$^{12}$ is lower alkyl or alkoxy having from 1 to 6 carbon atoms); pharmaceutically acceptable metal and amine cations means lithium, sodium, potassium, magnesium, calcium, aluminum, zinc, iron, copper, gold, ammonium, ethylenediamine, mon-, di- and triethanolamine, ethyldiethanolamine, n-butylethanolamine, 2-amino-2-methyl-1-propanol, tris(hydroxymethyl)-aminomethane, lysine, galactamine, N-methylglucosamine and the like.

DETAILED DESCRIPTION

The following reactionscheme illustrates the preparation of many of the compounds of the present invention:

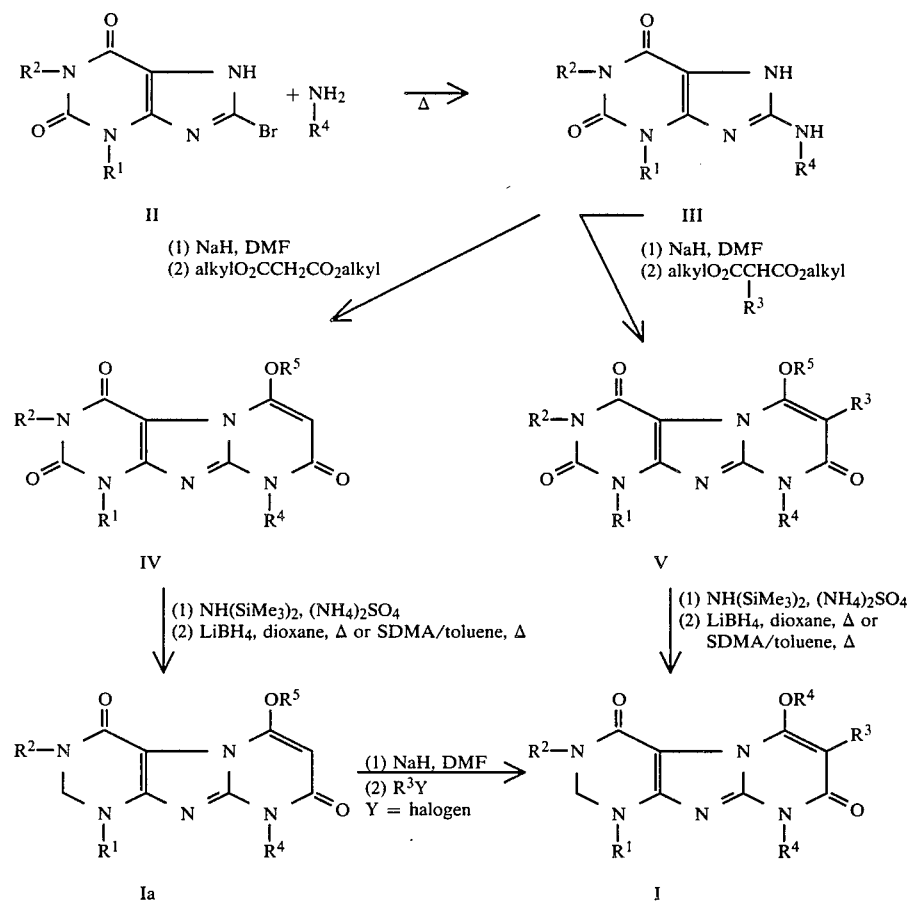

wherein R$^1$, R$^2$ and R$^3$ are as defined above.

When the desired substituents at R$^1$, R$^2$, R$^3$ and/or R$^4$ are not sensitive to lithium borohydride reduction, the R$^3$ substituted-2-desoxy compounds (I) may be prepared by direct reduction of the corresponding R$^3$-substituted-2-oxo compounds (V).

The intermediates of the invention having structural formula V wherein R$^5$=H and

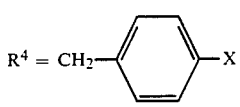

and X=H or F may be prepared by reacting a correspondingly substituted compound having structural formula III with a suitably substituted dialkylmalonate in the presence of a stoichiometric amount of a base such as sodium hydride at an elevated temperature. Also the above defined intermediates of formula V may be prepared by reacting the above defined compound of formula III with an excess of suitably substituted dialkylmalonate in the presence of a base such as sodium methoxide at an elevated temperature.

Alternatively, when one of the desired substituents at $R^3$ is sensitive to lithium borohydride reduction, the 2-oxo-$R^3$-unsubstituted compounds (IV) may be reduced to the $R^3$-unsubstituted-2-desoxy compounds (Ia) and the $R^3$ substituent sensitive to lithium borohydride reduction may be introduced subsequently by alkylation to produce the $R^3$ substituted-2-desoxy compounds (I).

The intermediates of the invention having structural formula IV wherein $R^5$=H and

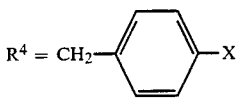

may be prepared by reacting a correspondingly substituted compound having structural formula III with a dialkylmalonate in the presence of a stoichiometric amount of a base such as sodium hydride at an elevated temperature. Also the above defined intermediates of formula IV may be prepared by reacting the above defined compound of formula III with an excess of dialkylmalonate in the presence of a base such as sodium methoxide at an elevated temperature.

Compounds having structural formula III are prepared by reacting compounds having structural formula II with excess primary amine at elevated temperatures.

Compounds having structural formula I wherein $R^3$=H and $R^5$=H or a sodium cation may be alkylated as shown in the reaction scheme above using activated electrophiles, e.g. such as 3-halo alkenes, 3-halo alkynes, α-halo esters, benzyl halides, α-halo acetonitriles and the equivalents of these groups which are known in the art. The alkylations may be accomplished using sodium hydride in N,N-dimethyl formamide, triethylamine in acetone and sodium or sodium methoxide in ethanol. Phase-transfer alkylation, employing a stoichiometric quantity of tetrabutyl ammonium hydrogen sulfate in a methylene chloride-aqueous sodium hydroxide system, is also effective.

$R^5$ alkyl derivatives may be conveniently prepared by a diazoalkane reaction.

The $R^3$-unsubstituted-2-desoxy compounds (Ia) and the $R^3$-substituted 2-desoxy compounds (I) may be prepared from the corresponding 2-oxo compounds by a novel reduction process using lithium borohydride in dioxane. The reaction times for this reduction process may in many cases be reduced significantly by silylation of the tricyclic 2-oxo compounds before they undergo reduction. The compound used in the silylation step may be 1,1,1,3,3,3-hexamethyldisilazane (HMDS).

Another metal hydride which may be used in the above novel reduction process is sodium bis(2-methoxyethoxy)aluminum hydride (SDMA) in dimethoxyethanetoluene. When SDMA is used, the yield and speed of direct reduction of underivatized substrate leading to compounds having structural formulas I and Ia may be comparable to those observed with LiBH4 on silylated substrates. However, SDMA should not be used to reduce those compounds having fluorinated aryl substituents.

The intermediates of formula III may be prepared from readily available starting materials according to the sequence of steps described below.

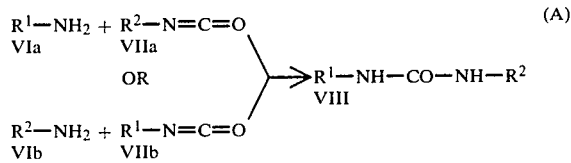

The ureas of formula VIII may be prepared by reacting approximately equimolar quantities of an amine ($R^1$—$NH_2$ or $R^2$—$NH_2$) with an isocyanate ($R^2$—N=C=O or $R^1$—N=C=O) in an inert solvent, e.g., chloroform.

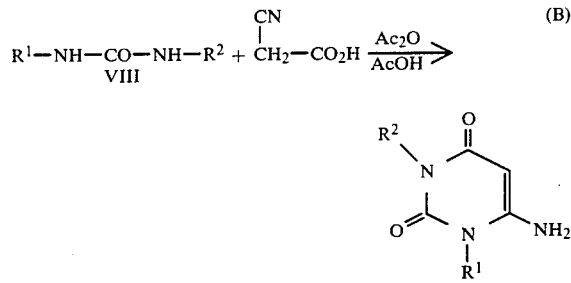

Compounds of formula IX may be prepared by the well known Traube purine synthesis or a modification thereof. Equimolar quantities of the compound of formula VIII and cyanoacetic acid are heated to 60° C. with two equivalents of acetic anhydride using glacial acetic acid as solvent. After 2 to 8 hours as much as possible of the acetic acid and acetic anhydride are removed at 60° C. in vacuo. The resultant mixture is poured into water and made basic, e.g., with solid sodium carbonate. The mixture is boiled 1–4 hours, then cooled. On standing either a solid will form which may be filtered off and purified, or an oil will form which may be extracted and purified.

Note that for compounds of formula VIII where $R^1$ and $R^2$ are different, two different compounds of formula IX may be formed, i.e.,

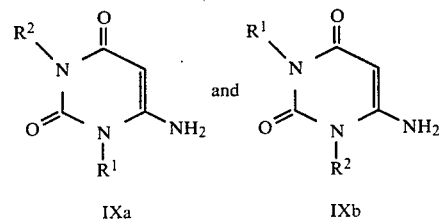

These compounds may be separated by fractional crystallization or by chromatography (e.g. column or HPLC).

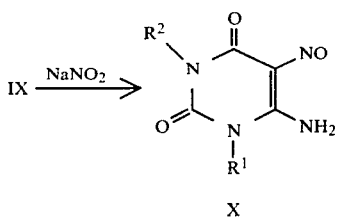

(C)

The purified 6-aminouracil compounds of formula IX may be converted to the 5-nitroso-6-aminouracil compounds of formula X by combining the 6-aminouracil derivative and sodium nitrite (one equivalent) and boiling in ethanol/ water while adding glacial acetic acid. The nitroso compound of formula X which precipitates is then filtered, washed with water and dried.

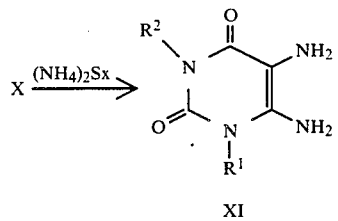

(D)

The 6-amino-5-nitrosouracil compound of formula X is reduced to the corresponding 5-amino-compound of formula XI in aqueous suspension by the use of an excess of ammonium polysulfide solution with warming. When the color is discharged, the mixture is cooled and the supernatant liquid is decanted off. The residue is dissolved in methylene chloride, which is dried and evaporated. The crude product is used in the next stop.

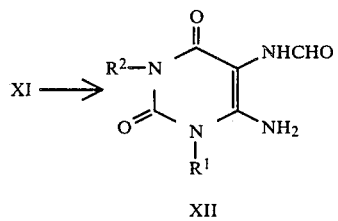

(E)

The 5,6-diaminouracil compound of formula XI is heated with excess formic acid at 120°–150° C. for 1–4 hours, then allowed to stand at room temperature overnight. Most of the acid is then removed (75° C.; reduced pressure) and the residue is dissolved in hot methanol and filtered. The product of formula XII is isolated by chilling and filtering off the resulting solid or by evaporation of the methanol.

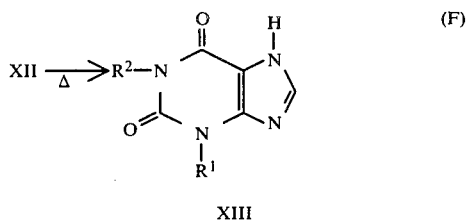

(F)

The 6-amino-5-formamidouracil compound of formula X is heated to 250°–285° C. until frothing ceases (10–60 mins.). The product is then cooled and the crude product of formula XIII is recrystallized, e.g. from MeOH/H$_2$O.

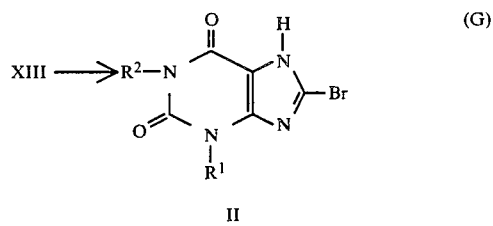

(G)

The xanthine compound of formula XIII is dissolved in glacial acetic acid. The solution is warmed gradually to 100° C. while a solution of bromine in acetic acid is slowly added until thin layer chromatography shows that starting material has been consumed. The product, a compound of formula II, is isolated by pouring the reaction mixture into water, filtering and recrystallizing, if necessary.

The 8-bromoxanthine of formula II is converted to the 8-substituted-amino-xanthine of formula III by heating with excess amine at elevated temperatures as described in preparative Example 1, below.

Compounds of the formula I wherein R$^5$ is hydrogen may exist in tautomeric forms.

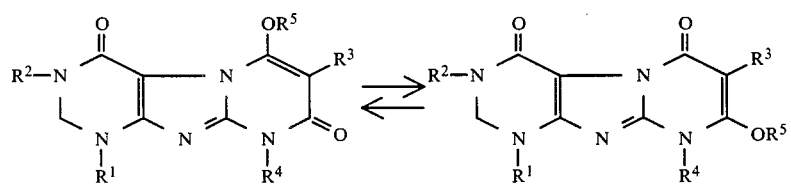

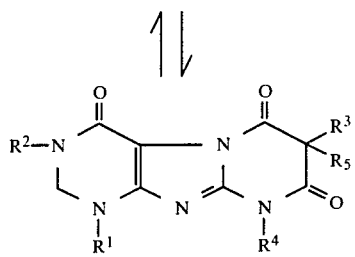

Such tautomeric forms are equivalent for purposes of the invention.

The following examples illustrate the preparation of the compounds and compositions of this invention.

PREPARATIVE EXAMPLE 1

8-Benzylamino-1,3-di-n-butyl-xanthine

Heat together a mixture of one equivalent of 8-bromo-1,3-di-n-butyl-xanthine with three to four equivalents of benzylamine at 160°–180° C. until thin layer chromatography analysis shows that no starting xanthine remains. Cool. Triturate with ethanol and water to yield 8-benzylamino-1,3-di-n-butyl-xanthine.

Similarly, prepare other 8-(substituted amino)-1,3-disubstituted xanthines required for the preparation of the compounds of the present invention from the corresponding 8-bromo-(or 8-chloro)-1,3-disubstituted xanthines by heating with excess amine at elevated temperatures, in a sealed vessel, if necessary.

PREPARATIVE EXAMPLE 2A

9-Benzyl-1,3-dimethyl-7-(2-ethoxyethyl)6-(hydroxy)-pyrimido[2,1-f]purine-2,4,8(1H,3H,9H)-trione (or tautomer)

To a stirred suspension of 7.43 g. of 8-benzyl-aminotheophylline in 104 ml of dry N,N-dimethyl-formamide add portionwise over 10 minutes 1.19 g. of a 60% dispersion of sodium hydride. Heat the mixture to 50° C. under a nitrogen atmosphere for 30 minutes. Add 13.30 g. of the diethyl ester of β-ethoxyethylmalonic acid. Heat the mixture to 150° C. under a nitrogen atmosphere for approximately 37 hours. Allow the system to cool to room temperature and remove the solvent in vacuo. Add a mixture of water:chloroform (1:2.5) to the resulting semisolid. Acidify the aqueous portion with 3M HCl. Extract the product from the aqueous portion with chloroform. Wash the chloroform extracts with brine, dry over anhydrous sodium sulfate, filter and remove the solvent in vacuo to give the crude product. Triturate the crude product with ether. Purify the crude product by column chromatography on silica gel and triturate the major fraction with hexane to give the title compound, m.p. 156.5°–157.5° C.

PREPARATIVE EXAMPLE 2B

9-Benzyl-1,3-dimethyl-6-hydroxy-7-(n-propyl) pyrimido[2,1-f]purine-2,4,8(1H,3H,9H)-trione (or tautomer)

Suspend 8-benzylamino-theophylline (10 g.) in diethyl n-propyl malonate (65 ml). Add sodium methoxide (0.7g.), and stir and heat to about 200° C. (bath temperature). Separate the ethanol which is formed with a Dean and Stark trap. After about 4 to 6 hours, raise the bath temperature to about 215° C. until no more starting material is present (as shown by thin layer chromatography).

Cool to below 60° C. and add ethanol. Stir and triturate and then filter, wash and air dry. Recrystallize the product from acetonitrile (about 60 parts). Wash with ether and dry in vacuo at 70° to 75° C. to yield the title compound having a melting point of 217° C. (yield about 62%).

PREPARATIVE EXAMPLE 3

1,3-Dimethyl-9-benzyl-6-methoxy-7-(n-propyl) pyrimido[2,1-f]purine-2,4,8(1H,3H,9H)-trione Dissolve 9-benzyl-1,3-dimethyl-6-hydroxy-7-(n-propyl)pyrimido[2,1-f]purine-2,4,8(1H,3H,9H)-trione (3 g.) in 200 ml chloroform at 0° and treat with an ethereal solution of diazomethane. Stir solution at 0° for 1.5 hours and destroy the excess diazomethane by the addition of acetic acid. Wash the chloroform solution with a solution of sodium bicarbonate and remove the chloroform under reduced pressure. Chromatograph the solid obtained on silica gel using 1% methanol in chloroform to give the title compound, m.p. 199°–201° C.

PREPARATIVE EXAMPLE 4

9-Benzyl-1,3-dimethyl-6-(hydroxy)pyrimido-[2,1-f]purine-2,4,8(1H,3H,9H)-trione

Add 8-benzylaminotheophylline (30 g.) and ethyl malonyl chloride (35.1 gm) to 600 ml of 1:1 dioxane/acetonitrile. Heat the reaction mixture to reflux under a nitrogen atmosphere until the 8-benzylaminotheophylline is consumed (Ca. 3.5 hrs.). Cool the reaction mixture to room temperature and pour the solution into 800 ml. of ether. Filter the precipitate. Wash the precipitate with ether and dry the product to obtain the title compound, m.p. 205.5°–209° C.

Similarly, prepare the following:
1,3-Dimethyl-9-(4-fluorobenzyl)-6-(hydroxy)-pyrimido[2,1-f]purine-2,4,8(1H,3H,9H)-trione.

EXAMPLE 1

9-BENZYL-2,3-DIHYDRO-1,3-DIMETHYL-6-HYDROXY-7-(PROPYL)PYRIMIDO[2,1-f]PURINE-4,8(1H,9H)-DIONE

A. Silylation. Reflux a mixture of 30.1 g. (0.076 mole) of 9-benzyl-1,3-dimethyl-6-hydroxy-7-(propyl)-pyrimido[2,1-f]purine-2,4,8(1H,3H,9H)-trione, 1.0 g. of ammonium sulfate and 350 ml. of 1,1,1,3,3,3-hexamethyldisilazane until the starting material dissolves, giving a cloudy solution. Distill the solvent under reduced pressure, and utilize the pinkish residual solid thus obtained directly in the reduction step "B".

B. Reduction. Dissolve the silylated product (approximately 0.076 mole) of step "A" in 1.3 liters of dry 1,4-dioxane. Place the reaction flask in a water bath at 15°–20° C., and cautiously add 9.59 g. (0.442 mole) of lithium borohydride portionwise to control the resultant frothing. Carefully (foaming) heat the reaction mixture to 90°–95° C. and maintain that temperature with effective stirring for 78 hours (disappearance of starting material may be monitored by TLC: silica; chloroform(80)-methanol(20)-concentrated ammonium hydroxide(1)).

Remove approximately one liter of dioxane by distillation under reduced pressure. Cool the residue to room temperature, and add 1 liter of chloroform. To the stirred mixture, cautiously add portionwise 200 ml. of water, followed by 180 ml. of 3M hydrochloric acid, and continue stirring for 0.5 hour. Separate the layers and extract the aqueous phase with two 200-ml. portions of chloroform. Dry the combined extracts over sodium sulfate, remove the drying agent by filtration and remove the solvent from the filtrate at reduced pressure. Chromatograph the solid thus obtained on silica gel, eluting first with ethyl acetate(75)-hexanes(25), then with ethyl acetate, to obtain the title compound with m.p. 173°–175° C. Recrystallize the chromatographed material to obtain product with m.p. 177°–178.5° C.

Sodium salt. To a stirred suspension of 12.66 g. (0.033 mole) of the chromatographed title compound in 1100 ml. of water, add a solution of 1.33 g. (0.033 mole) of sodium hydroxide in 400 ml. of water. Stir for 5 hours; then filter the hazy, fine suspension through medium sintered glass. Lyophilize the clear filtrate to obtain the title salt as a solid. If the solid thus obtained is gummy, dissolve it in methanol; then remove methanol under reduced pressure, and triturate the residual solid with ether(1)-hexanes(3). Filter, and dry the product at 40° C. under vacuum to obtain the sodium salt of the title compound as a ¾ hydrate with m.p. 215° C. (dec.).

Alternatively, preparation of the title compound may be carried out as follows:

To a stirred suspension of 0.5 g. (1.27 mmoles) of 9-benzyl-2,3-dihydro-1,3-dimethyl-6-hydroxy-7-(propyl)pyrimido-[2,1-f]purine-2,4,8(1$\underline{H}$,3$\underline{H}$,9$\underline{H}$)-trione in a mixture of 32 ml. of dry dimethoxyethane and 12 ml. of dry toluene, cautiously add 1.5 ml. (5.1 mmoles) of a 3.4M solution of sodium bis(2-methoxyethoxy)aluminum hydride in toluene. Reflux the resultant mixture under a nitrogen atmosphere for 16 hours. Remove solvent under reduced pressure, and stir the residual oil under nitrogen with 20 ml. of ether and 25 ml. of 1.5M hydrochloric acid. Separate the layers, and extract the aqueous phase with two 20-ml. volumes of ether. Dry the combined extracts over magnesium sulfate, filter off the drying agent and remove solvent from filtrate under reduced pressure. Purify the residual solid chromatographically, as described above, to obtain the title compound.

EXAMPLE 2

9-Benzyl-2,3-dihydro-1,3-dimethyl-6-hydroxy-7-(3-methyl-2-butenyl)pyrimido[2,1-f]purine-4,8(1$\underline{H}$,9$\underline{H}$)-dione Step A: 9-Benzyl-2,3-dihydro-1,3-dimethyl-6-(hydroxy)pyrimido[2,1-f]purine-4,8(1$\underline{H}$,9$\underline{H}$)-dione (I).

To a suspension of 395 g. (1.12 moles) of 9-benzyl-1,3-dimethyl-6-(hydroxy)pyrimido[2,1-f]purine-2,4,8(1$\underline{H}$,3$\underline{H}$,9$\underline{H}$)-trione in 10.5 liters of dry 1,4-dioxane, add 68.1 g. (3.14 moles) of lithium borohydride in portions. Maintain the reaction temperature at 20°–25° C. by controlling the rate of addition and by use of a cooling bath as needed. Stir the mixture at room temperature for 0.5 hour, then reflux for 18 hours. Remove solvent under reduced pressure. Allow the residue to cool; then add 4.5 liters of chloroform. To the resultant mixture, cautiously add dropwise 1.1 liters of water. Stir the mixture at room temperature until two clear phases result. Add 3N hydrochloric acid portionwise to bring the pH to 4–5. Separate the layers, and extract the aqueous phase with two 1.1-liter portions of chloroform. Wash the combined extracts with three 1.1-liter volumes of water, and dry over anhydrous sodium sulfate. Filter the drying agent, and remove volatiles from the filtrate under reduced pressure. Crystallize the residue from methanol-ethyl acetate to obtain title compound (I) as a solid with m.p. 176°–182° C.

Step B: Alkylation of I.

To a suspension of 75 g. (0.221 mole) of I in 4.2 liters of ethanol (anhydrous; 2B) add 12 g. (0.221 mole) of sodium methoxide portionwise during about twenty minutes. To the resultant mixture add 33 g. (0.221) mole of 1-bromo-3-methyl-2-butene dropwise during 0.5 hour. Stir the reaction mixture for 18 hours at room temperature; then remove volatiles under reduced pressure. Pour the residue into 8.8 liters of cold water, saturate the aqueous phase with sodium chloride and extract with three 3-liter volumes of ether. Dry the combined extracts over anhydrous sodium sulfate, filter out the drying agent and remove solvent from the filtrate under reduced pressure. Chromatograph the residue on silica gel, eluting with ethyl acetate(3)-hexanes(2), to obtain the title compound as a solid with m.p. 153°–154.5° C.

Alternatively, the alkylation of I may be carried out in the following manner: To a slurry of 0.85 g. (0.0212 mole) of 60% sodium hydride (prewashed with hexanes) in 5 ml. of dry N,N-dimethylformamide, add in two portions a solution of 6.11 g. (0.018 mole) of I in 125 ml. of dry N,N-DMF. Stir the mixture at room temperature under a nitrogen atmosphere for 15 minutes to obtain a clear solution. Add in one portion 4.06 g. (0.0273 mole) of 1-bromo-3-methyl-2-butene (mild exotherm). Stir the reaction mixture under a nitrogen atmosphere at room temperature for 4.5 hours. Pour the reaction mixture into an ice-water mixture, and extract with four 150-ml. portions of chloroform. Wash the combined extracts with water, dry (anhydrous sodium sulfate), evaporate solvent, and chromatograph the residue on silica gel, as described above, to obtain the title compound.

EXAMPLE 3

2,3-Dihydro-1,3-dimethyl-9-(4-fluorobenzyl)-6-(hydroxy)pyrimido[2,1-f]purine-4,8(1$\underline{H}$,9$\underline{H}$)-dione Reflux a suspension of 395 g. (1.06 moles) of 1,3-dimethyl-9-(4-fluorobenzyl)-6-(hydroxy)pyrimido[2,1-f]purine-2,4,8(1$\underline{H}$,3$\underline{H}$,9$\underline{H}$)-trione, 12.32 g. of ammonium sulfate and 350 ml. of 1,1,1,3,3,3-hexamethyldisilazane in 4 liters of chloroform until a clear solution is obtained (18–24 hr.). Remove chloroform and excess hexamethyldisilazane under reduced pressure, and treat the residual thick gum with 9.6 liters of dry 1,4-dioxane. While stirring the resultant mixture, cautiously add 70.4 g. (3.24 moles) of lithium borohydride in portions under a stream of dry nitrogen. When foaming subsides, heat the mixture to 100° C. for 18 hr. or until all starting material has been consumed (as determined by TLC: silica; chloroform(90)-methanol(10)-acetic acid(1)). Remove dioxane under reduced pressure, and stir the residue with 3 liters of chloroform. Cautiously (foaming) add 1.3 liters of water, followed by 2.3 liters of 3N hydrochloric acid. Stir for one hour; then separate the layers. Extract the aqueous phase with two 1.3-liter volumes of chloroform, and dry the combined extracts over anhydrous sodium sulfate. Filter the drying agent, and remove solvent from the filtrate under reduced pressure. Dissolve the residual tacky solid in 1.5 liters of boiling acetonitrile, add a small amount of decolorizing carbon, reflux for 15 minutes, and filter through a pad of Celite. Chill the filtrate, and collect the resultant crystals. Wash the crystals with cold acetonitrile, and dry them under vaccuum at 50° C. to obtain the title compound wth m.p. 214°-232° C.

When the above reduction was attempted to obtain the title compound without pretreatment of the substrate with 1,1,1,3,3,3, hexamethyldisilazane, no reaction was observed after 6 days of reflux.

EXAMPLE 4

2,3-Dihydro-1,3-dimethyl-9-(4-fluorobenzyl)-6-hydroxy-7-(3-methyl-2-butenyl)pyrinido[2-1-f]purine-4,8(1H,9H)-dione Dissolve 1.48 g. (0.0644 mole) of sodium metal in 450 ml. of ethanol (SD2B; anhydrous). Add 23.0 g. (0.0644 mole) of 2,3-dihydro-1,3-dimethyl-9-(4-fluorobenzyl)-6-(hydroxy)pyrimido[2,1-f]purine-4,8(1H,9H)-dione. Stir the resultant suspension under a nitrogen atmosphere for 0.5 hour, then add 9.60 g. (0.0644 mole) of 1-bromo-3-methyl-2-butene. Stir the mixture at room temperature for 90 hours under a nitrogen atmosphere. Filter the white solids, and remove solvent from the filtrate under reduced pressure. Dissolve the residue in 150 ml. of chloroform, add 125 ml. of 3N hydrochloric acid and shake the mixture. Separate the layers, and extract the aqueous phase with two 50-ml. volumes of chloroform. Dry the combined extracts over anhydrous magnesium sulfate, filter off the drying agent, and remove solvent from the filtrate under reduced pressure. Chromatograph the residual glassy solid on silica gel, eluting with ethyl acetate(3)-hexanes(1). Triturate the product thus obtained with hexane (125 ml. per gram) and filter to obtain the title compound as a solid with m.p. 188°-188.5° C.

EXAMPLE 5

7,9-Dibenzyl-2,3-dihydro-1,3-dimethyl-6-(hydroxy)-pyrimido[2,1-f]purine-4,8(1H,9H)-DIONE To a suspension of 7.1 g. (0.021 mole) of 9-benzyl-2,3-dihydro-1,3-dimethyl-6-(hydroxy)pyrimido[2,1-f]purine-4,8(1H,9H)-dione in 200 ml. of acetone, add 2.3 g. (0.023 mole) of triethylamine, and stir the mixture for 5 minutes at room temperature under a nitrogen atmosphere to obtain a clear solution. Add dropwise to the solution 4.7 g. (0.027 mole) of benzyl bromide, and reflux the mixture for 5 hours under a nitrogen atmosphere. Remove the acetone under reduced pressure, and triturate the gummy residue with methanol. Remove the resultant white solid by filtration, pour the filtrate into water, acidify to pH 4-5 with dilute hydrochloric acid, and decant the aqueous supernatant. Dissolve the gummy residue in the chloroform, wash the solution with water, and dry over anhydrous magnesium sulfate. Remove the drying agent by filtration, and evaporate solvent from the filtrate under reduced pressure. Chromatograph the residual oil on silica gel, eluting with chloroform(96)-methanol(4), to obtain the title compound as a solid with m.p. 176°-179° C.

Sodium salt. To a suspension of 0.5 g. (0.012 mole) of 60% sodium hydride (prewashed with three 100-ml. volumes of petroleum ether) in 300 ml. of dry dimethoxyethane, add 3.4 g.(0.0079 mole) of analytically pure 7,9-dibenzyl-2,3-dihydro-1,3-dimethyl-6-(hydroxy)-pyrimido[2,1-f]purine-4,8(1H,9H)-dione. Stir the mixture for 30 minutes at room temperature under a nitrogen atmosphere. Filter off excess sodium hydride. Concentrate the filtrate under reduced pressure to an oil and add ether to precipitate a solid. Isolate the solid by filtration, and triturate it in fresh ether. Filter again, and dry the solid at 70° C. under reduced pressure to obtain the hemihydrate salt of the title compound as a yellow powder with m.p. 175°-185° C.

The compounds of this invention can be used to treat inflammatory conditions such as arthritis, spondylitis and tendonitis and are conventionally formulated for oral, parenteral, topical and transdermal use.

The anti-inflammatory potential of the compounds of the present invention may be determined by the Prophylactic Adjuvant-Induced Arthritis in Rats (AAR) technique as set forth below.

Of course, the dosage regimen and amount to be administered and mode of administration depends upon the judgement of the attending clinician considering the potency of the particular compound used, the age and general health of the patient and the severity of the inflammatory condition. Generally the recommended regimen is a dosage range of about 1 milligram per kilogram of body weight per day to about 50 milligrams per kilogram of body weight per day in divided doses taken at about 4 hour intervals.

Prophylactic Adjuvant-Induced Arthritis in Rats (AAR)

Groups of 10 male Lewis rats (from Charles River Laboratories, Ma.), weighing 150-170 grams are sensitized by subplantar injection in the left hind paw with 0.1 ml Freund's complete adjuvant enriched with heat-killed tuberculin bacilli. Hind paw volumes are determined with a mercury plethysmograph on Day 0 and 21 of the study. Differences in paw volume on Day 0 and 21 are recorded as the delta ($\Delta$) paw volume. In sensitized rats the injected hind paw increases in size by Day 2 while seven days later a similar response is seen in the contralateral hind paw. Differences in body weights on Day 0 and Day 21 are recorded as the delta ($\Delta$) body weight gain.

Daily oral doses of the drug suspended in methylcellulose or the methylcellulose alone, are administered from Day 0 to Day 21.

The compounds of this invention are also useful for the treatment of allergy caused diseases and their preferred use is for treating allergic chronic obstructive lung diseases. Chronic obstructive lung disease as used herein means disease conditions in which the passage of air through the lungs is obstructed or diminished such as is the case in asthma, bronchitis and the like.

The compounds of this invention can be administered in unit dosage forms such as tablets, capsules, pills, powders, granules, sterile parenteral solutions or suspensions, mechanical delivery devices, e.g., transdermals and the like. In whatever form the compounds are dispensed, they may be admixed with the pharmaceutically acceptable excipients, binders, dispersing agents and carriers generally used in the art.

Exemplary of the pharmaceutical carriers, excipients, preservatives and binders are gelatin, lactose, starch, magnesium stearate, talc, vegetable oils, gums, polyalkylene glycols, etc. The pharmaceutical dosage forms are prepared by the methods conventionally used in the art. Further, the dosage units may also contain a compatible anti-depressant and/or analgesics to treat the depression and pain usually associated with chronic inflammatory conditions.

The following examples illustrate the preparation of solid dosage forms:

| A. Capsules: | | | |
|---|---|---|---|
| No. | Ingredient | mg/capsule | mg/capsule |
| 1. | Compound of the invention | 50 | 250 |
| 2. | Lactose USP | 50 | 100 |
| 3. | Corn Starch, Food Grade | 48.5 | 50 |
| 4. | Microcrystalline Cellulose NF | 50 | 95 |
| 5. | Magnesium Stearate NF | 1.5 | 5 |
| | Total | 200 | 500 |

Method of Manufacture

Mix Item Nos. 1, 2, 3 and 4 in a suitable mixer for 10-15 minutes. Add Item No. 5 and mix for 1-3 minutes. Fill the mixture into suitable two-piece hard gelatin capsules using encapsulating machine.

| B. Tablets: | | | |
|---|---|---|---|
| No. | Ingredient | mg/capsule | mg/capsule |
| 1. | Compound of the invention | 50 | 250 |
| 2. | Lactose USP | 68 | 57 |
| 3. | Corn Starch, Food Grade, as a 10% paste in Purified Water | 10 | 20 |
| 4. | Corn Starch, Food Grade | 20 | 18 |
| 5. | Magnesium Stearate NF | 2 | 5 |
| | Total | 150 | 350 |

Method of Manufacture

Mix Item Nos. 1 and 2 in a suitable mixer for 10-15 minutes. Granulate the mixture with Item No. 3. Pass if needed, and dry the wet granules. Mill the dried granules. Combine Item No. 4 and the dried granules and mix for 10-15 minutes. Add Item No. 5 and mix for 1-3 minutes. Compress the mixture to appropriate size and weight on a suitable tablet machine.

We claim:

1. A compound having the structural formula I

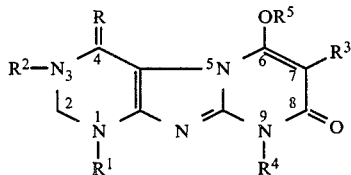

its tautomers, pharmaceutically acceptable salts or hydrates wherein $R^1$ and $R^2$ are independently selected from hydrogen, cycloalkyl having from 3 to 8 carbon atoms, phenyl, substituted phenyl and lower alkyl [which may be substituted with cycloalkyl having from 3 to 8 carbon atoms, phenyl, thienyl or substituted phenyl];

$R^3$ is hydrogen, formyl, cycloalkyl having from 3 to 8 carbon atoms, alkenyl having from 2 to 8 carbon atoms which alkenyl may be substituted with up to 6 fluorines, alkynyl having from 3 to 8 carbon atoms, cycloalkenyl having from 5 to 8 carbon atoms, acyloxyalkyl having from 2 to 12 carbon atoms, $X-R^6$ [wherein X is O, N or S and $R^6$ is phenyl, substituted phenyl or alkyl having from 1 to 6 carbon atoms (which may be substituted with cycloalkyl having from 3 to 8 carbon atoms or phenyl)],-alkylY-$C_pH_{2p+1}$ [wherein the alkyl portion has 1 to 6 carbon atoms, p is an integer from 0 to 4, and Y represents CO, O, S, $S^+-O^-$, $SO_2$ or $-NC_rH_{2r+1}$ wherein r is an integer from 0 to 4], $-(CH_2)_nCONR^7R^8$ [wherein $R^7$ and $R^8$ are independently hydrogen or lower alkyl and n is an integer from 0 to 6], $-(CH_2)_mC(O)OR^9$ [wherein $R^9$ is hydrogen, lower alkyl or a pharmaceutically acceptable metal or amine cation and m is an integer from 0 to 6], phenyl, substituted phenyl or lower alkyl [which may be substituted with hydroxy, sulfhydryl, cyano, amino, halo, cycloalkyl having from 3 to 8 carbon atoms, phenyl, thienyl and substituted phenyl];

$R^4$ is hydrogen, phenyl, thienyl, and substituted phenyl, lower alkyl [which may be substituted with cycloalkyl having from 3 to 8 carbon atoms, phenyl, thienyl or substituted phenyl]; and $R^5$ is hydrogen, alkyl having from 1 to 4 carbon atoms or a pharmaceutically acceptable metal or amine cation.

2. A compound defined in claim 1 having the structural formula I and the pharmaceutically acceptable salts thereof, wherein $R^1$ and $R^2$ are independently selected from alkyl of 1 to 4 carbon atoms;

$R^3$ is hydrogen, alkenyl having from 2 to 8 carbon atoms which alkenyl may be substituted with up to 6 fluorines, alkynyl having from 3 to 8 carbon atoms, cycloalkenyl having from 5 to 8 carbon atoms or lower alkyl which may be substituted with phenyl; $R^4$ is lower alkyl [which is substituted with either phenyl, thienyl or substituted phenyl]; and $R^5$ is hydrogen or a pharmaceutically acceptable cation.

3. A compound defined in claim 1 wherein $R^1$ and $R^2$ are alkyl of 1 to 3 carbon atoms.

4. A compound defined in claim 1 wherein $R^1$ and $R^2$ are methyl.

5. A compound defined in claim 1 wherein $R^3$ is hydrogen, alkenyl having from 3 to 8 carbon atoms which alkenyl may be substituted with up to 6 fluorines, alkynyl having from 3 to 8 carbon atoms, cycloalkenyl having from 5 to 8 carbon atoms or lower alkyl which may be substituted with phenyl.

6. A compound defined in claim 1 wherein $R^3$ is hydrogen, methyl, n-propyl, propargyl [$-CH_2C\equiv CH$], allyl, trans-2-butenyl, 2-cylohexenyl, prenyl [$-CH_2CH=C(CH_3)_2$], $-CH_2CH=C(CF_3)CH_3$, $-CH_2CH=C(CF_3)_2$ or benzyl.

7. A compound defined in claim 1 wherein $R^4$ is benzyl or substituted benzyl.

8. A compound defined in claim 1 wherein $R^4$ is benzyl, p-fluorobenzyl or 2-thienylmethyl.

9. A compound defined in claim 3 wherein $R^3$ is hydrogen, alkenyl having from 3 to 8 carbon atoms which alkenyl may be substituted with up to 6 fluorines, cycloalkenyl having from 5 to 8 carbon atoms, alkynyl having from 3 to 8 carbon atoms or lower alkyl which may be substituted with phenyl.

10. A compound defined in claim 9 wherein $R^3$ is hydrogen, methyl, n-propyl, propargyl, allyl, prenyl, —CH$_2$CH=C(CF$_3$)CH$_3$, —CH$_2$CH=C(CF$_3$)$_2$ or benzyl.

11. A compound defined in claim 9 wherein $R^4$ is benzyl or substituted benzyl.

12. A compound defined in claim 9 wherein $R^4$ is benzyl, p-fluorobenzyl or 2-thienylmethyl.

13. A compound defined in claim 10 wherein $R^4$ is benzyl, substituted benzyl or 2-thienylmethyl.

14. A compound defined in claim 10 wherein $R^4$ is benzyl, p-fluorobenzyl or 2-thienylmethyl.

15. A compound defined in claim 1 selected from the group consisting of:
9-benzyl-2,3-dihydro-1,3-dimethyl-6-hydroxy-7-(propyl)pyrimido-[2,1-f]purine-4,8-(1H,3H,9H)-dione;
2,3-dihydro-1,3-dimethyl-9-(4-fluorobenzyl)-6-hydroxy-7-(propyl)pyrimido-(2,1-f]purine-4,8(1H,9H)-dione;
9-benzyl-2,3-dihydro-1,3-dimethyl-6-hydroxy-7-(3-methyl-2-butenyl)pyrimido-[2,1-f]purine-4,8(1H,9H)-dione;
9-benzyl-2,3-dihydro-1,3-dimethyl-6-(hydroxy)-pyrimido[2,1-f]purine-4,8-(1H,9H)-dione;
2,3-dihydro-1,3-dimethyl-9-(4-fluorobenzyl)-6-hydroxy-7-(3-methyl-2-butenyl)pyrimido[2,1-f]purine-4,8(1H,9H)-dione;
9-benzyl-2,3-dihydro-1,3-dimethyl-6-hydroxy-7-(methyl)-pyrimido[2,1-f]purine-4,8(1H, 9H)-dione;
2,3-dihydro-1,3-dimethyl-9-(4-fluorobenzyl)-6-(hydroxy)pyrimido[2,1-f]purine-4,8(1H,9H)-dione;
7,9-dibenzyl-9-benzyl-2,3-dihydro-1,3-dimethyl-6-(hydroxy)pyrimido[2,1-f]purine-4,8(1H,9H)-dione;
9-benzyl-2,3-dihydro-1,3-dimethyl-7-formyl-6-(hydroxy)pyrimido[2,1-f]purine-4,8(1H,9H)-dione;
2,3-dihydro-1,3-dimethyl-9-(4-fluorobenzyl)-6-hydroxy-7-(2-propenyl)pyrimido[2,1-f]purine-4,8(1H,9H)-dione;
9-benzyl-2,3-dihydro-1,3-dimethyl-7-(2-propynyl)-6-(hydroxy)oyrimido[2,1-f]purine-4,8(1H,9H)-dione
9-benzyl-7-(trans-2-butenyl)-2,3-dihydro-1,3-dimethyl-6-(hydroxy)pyrimido[2,1-f]purine-4,8(1H,9H)-dione;
9-benzyl-7-(3-cyclohexenyl)-2,3-dihydro-1,3-dimethyl-6-(hydroxy)pyrimido[2,1-f]purine-4,8 (1H,9H)-dione;
9-benzyl-2,3-dihydro-1,3-dimethyl-7-(ethoxy carbonylmethyl)-6-(hydroxy)pyrimido[2,1-f]purine-4,8(1H,9H)-dione;
2,3-dihydro-1,3-dimethyl-9-(2-thienylmethyl)-6-hydroxy-7-propylpyrimido[2,1-f]purine-4,8(1H,9H)-dione; or
2,3-dihydro-1,3-dimethyl-9-(4-methoxybenzyl)-6-hydroxy-7-(3-methyl-2-butenyl)pyrimido[2,1-f]purine-4,8(1H,9H)-dione.

16. A method for preparing a compound having the structural formula I as defined in claim 1 which comprises:
(a) reacting a compound having the structural formula

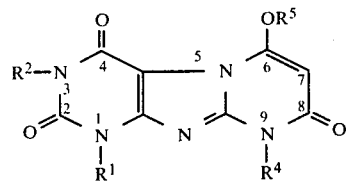

wherein $R^1$, $R^2$, $R^4$ and $R^5$ are defined in claim 1 with a suitable reducing agent;
(b) reacting the product produced in (a) having the structural formula

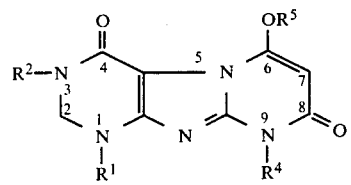

wherein $R^1$, $R^2$, $R^4$ and $R^5$ are defined in claim 1 with an activated electrophile and recovering the resulting product.

17. The process of claim 16 wherein the suitable reducing agent is lithium borohydride or sodium bis (2-methoxyethoxy) aluminum hydride provided that sodium bis (2-methoxyethoxy) aluminum hydride is not used to reduce compounds having fluorinated aryl substituents.

18. The process of claim 16 wherein the activated electrophile is 3-halo alkene, 3-halo alkyne, α-halo ester, benzyl halide or α-halo acetonitrile.

19. A method for preparing a compound having the structural formula I as defined in claim 1 which comprises reacting a compound having the structural formula

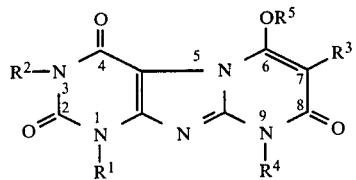

wherein $R^1$, $R^2$, $R^3$, $R^4$ and $R^5$ are defined in claim 1 with a suitable reducing agent and recovering the resulting product.

20. The process of claim 19 wherein the suitable reducing agent is lithium borohydride or sodium bis (2-methoxyethoxy) aluminum hydride provided that sodium bis (2-methoxyethoxy) aluminum hydride is not used to reduce compounds having fluorinated aryl substituents.

21. The compounds defined in claim 15 in the form of their tautomers, sodium salts or hydrates.

22. A pharmaceutical composition which comprises a compound having structural formula I as defined in claim 1 in combination with a pharmaceutically acceptable carrier.

23. A method for treating inflammation in a mammal which comprises administering an anti-inflammatory effective amount of the pharmaceutical composition defined in claim 22 to said mammal.

24. A method for treating allergic reactions in a mammal which comprises administering an anti-allergic effective amount of the pharmaceutical composition defined in claim 22 to said mammal.

* * * * *

UNITED STATES PATENT AND TRADEMARK OFFICE
CERTIFICATE OF CORRECTION

PATENT NO. : 4,666,914
DATED : May 19, 1987
INVENTOR(S) : Solomon, Daniel M. et. al.

It is certified that error appears in the above—identified patent and that said Letters Patent is hereby corrected as shown below:

In the Claims:

Col 17, line 48: delete

[(hydroxy)oyrimido[2,1-f] purine-4,8(1$\underline{H}$,9$\underline{H}$)-dione]

and insert:

(hydroxy)pyrimido[2,1-f]purine-4,8(1H,9H)-dione.

Signed and Sealed this

Fifteenth Day of September, 1987

*Attest:*

DONALD J. QUIGG

*Attesting Officer*     *Commissioner of Patents and Trademarks*